United States Patent
Ritter

(10) Patent No.: US 9,427,511 B2
(45) Date of Patent: Aug. 30, 2016

(54) HEMODIALYSIS SALT CONTAINER WITH VENTILATION

(75) Inventor: Ralf Ritter, Untermeitingen (DE)

(73) Assignee: RiTTER GMBH, Kaufbeuren (DE)

( * ) Notice: Subject to any disclaimer, the term of this patent is extended or adjusted under 35 U.S.C. 154(b) by 2817 days.

(21) Appl. No.: 11/639,004

(22) Filed: Dec. 14, 2006

(65) Prior Publication Data

US 2007/0138183 A1    Jun. 21, 2007

(30) Foreign Application Priority Data

Dec. 15, 2005    (DE) .................. 10 2005 060 290

(51) Int. Cl.
| | | |
|---|---|---|
| *B65D 51/16* | (2006.01) | |
| *B65D 83/70* | (2006.01) | |
| *A61M 37/00* | (2006.01) | |
| *A61M 1/16* | (2006.01) | |
| *A61M 39/24* | (2006.01) | |

(52) U.S. Cl.
CPC ......... *A61M 1/1656* (2013.01); *A61M 1/1666* (2014.02); *A61M 1/1668* (2014.02)

(58) Field of Classification Search
CPC ... B65D 51/16; B65D 83/70; A61M 1/1652; A61M 1/1631; A61M 2039/242
USPC .......... 220/203.08, 366.1, 231, 203.18, 89.2; 604/4.01, 5.01, 6.09, 6.11, 29, 6.1
See application file for complete search history.

(56) References Cited

U.S. PATENT DOCUMENTS

| | | | | |
|---|---|---|---|---|
| 2,440,462 A | * | 4/1948 | Cooper | 220/89.3 |
| 4,115,629 A | * | 9/1978 | Dey et al. | 429/56 |
| 4,366,051 A | * | 12/1982 | Fischel | 210/96.2 |
| 5,045,077 A | * | 9/1991 | Blake, III | 604/321 |
| 5,908,129 A | * | 6/1999 | Schutz | 220/203.11 |
| 6,866,056 B1 | * | 3/2005 | Scott | 137/15.18 |

FOREIGN PATENT DOCUMENTS

| | | |
|---|---|---|
| DE | 696 16 073 | 1/1997 |
| DE | 101 00 549 | 7/2002 |
| EP | 0 112 295 | 6/1984 |
| WO | WO 99/06083 | 2/1999 |

* cited by examiner

*Primary Examiner* — Fenn Mathew
*Assistant Examiner* — Andrew T Kirsch
(74) *Attorney, Agent, or Firm* — Klaus J. Bach

(57) ABSTRACT

In a rigid hemodialysis salt container of plastic material including a venting valve formed in a container wall with a venting opening extending through the container wall, a seal member covers the venting opening at the inside of the container wall and is connected to the container wall by cementing or welding such that, with the occurrence of a predetermined pressure difference between ambient air pressure and a vacuum generated in the container, the seal member is at least locally ripped off.

6 Claims, 3 Drawing Sheets

HEMODIALYSIS SALT CONTAINER WITH VENTILATION

BACKGROUND OF THE INVENTION

The invention resides in a rigid salt container of plastic material for the hemodialysis which is sealed in an airtight manner and includes a coupling arrangement for communication with a dialysis apparatus.

Such containers are one-way devices which contain the amount of bicarbonate salt required for a hemodialysis procedure and which, during use, are connected to a hemodialysis apparatus by way of the coupling arrangement. The hemodialysis apparatus then conducts dialysis liquid through the salt container for the absorption of the salt.

Such salt containers are known in the form of flexible bags (for example WO 99/06083A1, DE 696 16 073 T2) and also in the form of rigid containers (for example, EP 0 112 295 A2).

At the end of the procedure, the dialysis apparatus sucks the dialysis liquid out of the salt container. With salt containers in the form of flexible bags, the bag is compressed because of the vacuum generated therein so that it is emptied without problems. With rigid containers, which have certain advantages over flexible bags, the emptying is problematic because the rigid container cannot collapse. As a result, the liquid can only be partially sucked out.

It is the object of the present invention to provide a rigid salt container for the hemodialysis in such a way that it can be emptied without problems by the vacuum generated by the dialysis apparatus.

SUMMARY OF THE INVENTION

In a rigid hemodialysis salt container of plastic material including a venting valve formed in a container wall with a venting opening extending through the container wall, a seal member covers the venting opening at the inside of the container wall and is connected to the container wall by cementing or welding such that, with the occurrence of a predetermined pressure difference between ambient air pressure and a vacuum generated in the container, the seal member is at least locally ripped off.

The vent valve which is designed taking into consideration that the salt container is a one-way container that is in such a way that it can be produced inexpensively and is accommodated in the container in an unobtrusive manner.

The invention will be described below in greater detail on the basis of particular embodiments which is shown in the accompanying drawings.

DESCRIPTION OF PARTICULAR EMBODIMENTS

Figure 1:
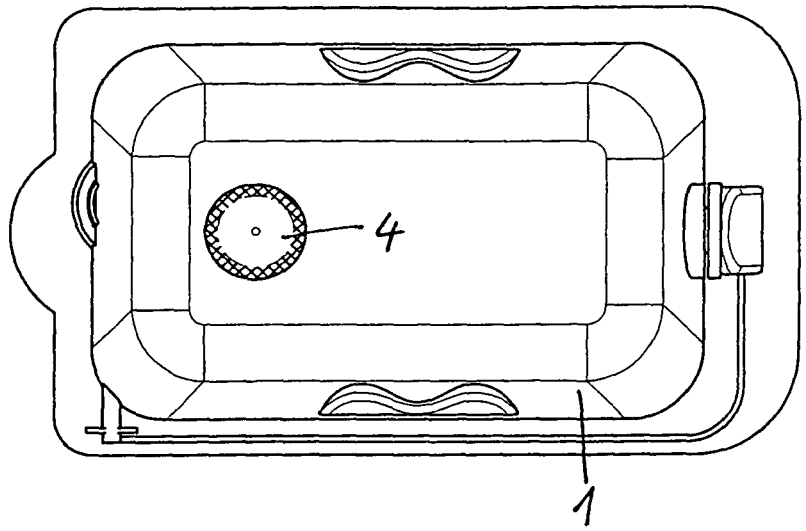
FIG. 1 is a top view of a rigid salt container according to the invention without cover.
Figure 2:
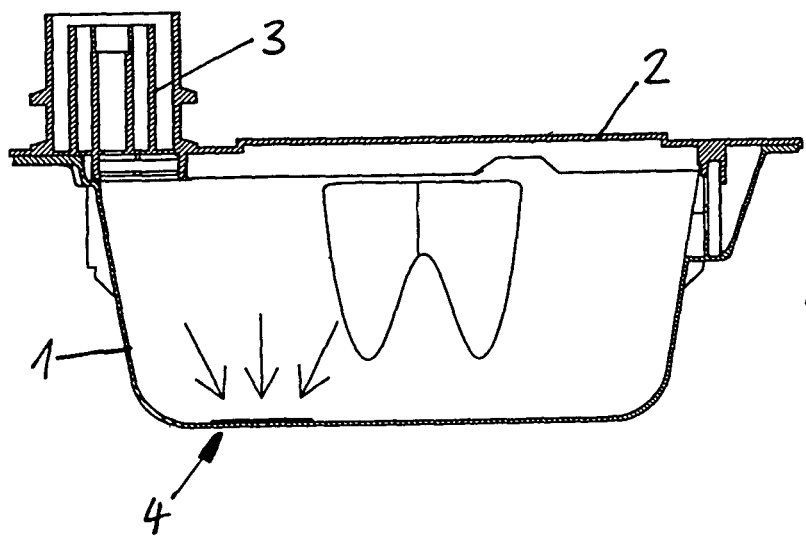
FIG. 2 is a longitudinal cross-sectional view of the container showing a seal member in a sealing position.

The FIGS. 1 and 2 show a rigid salt container consisting of a tub-shaped bottom part 1, a cover 2 and a co-axial plug-in coupling disposed on the cover 2. All these parts are visible in the cross-sectional view of FIG. 2. In the top view of FIG. 1, only the bottom part 1 without cover is shown. The salt filling is not shown. When filled and ready for use, the bottom part 1 and the cover part 2 of the salt container are welded together.

The construction of the bottom part, the cover and the co-axial plug-in coupling are known per se and will therefore not be described in detail.

The bottom part 1 is provided with a venting valve 4 arranged at the bottom wall in order to facilitate the total emptying of the salt container when the dialysis liquid is sucked out of the container after the salt filling is flushed out of the salt container connected to a dialysis apparatus by permitting ambient air to enter when a vacuum is formed in the container.

It is essential that such a venting valve for a one-way salt container is easy and inexpensive to manufacture and that it operates reliably.

Figure 3:
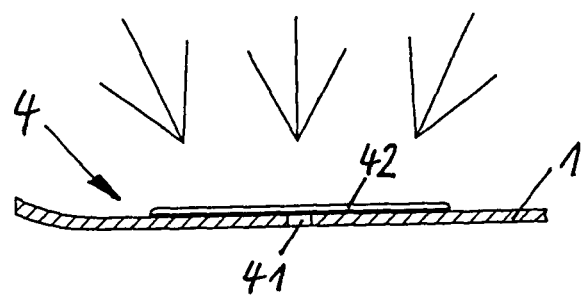
FIG. 3 is an enlarged representation of the seal areas of FIG. 2 with the seal member closed.

As apparent from FIG. 3, the venting valve 4 comprises an opening 41 formed in the bottom wall of the bottom part 1 and a seal member 42 provided at the inside of the bottom wall so as to close the opening 41. As shown in FIG. 1, the seal member consists of a foil which is cemented or welded by ultrasound to the bottom wall along a circle around the opening 41. In FIG. 1, the annular attachment area is indicated by cross-hatching.

Figure 4:
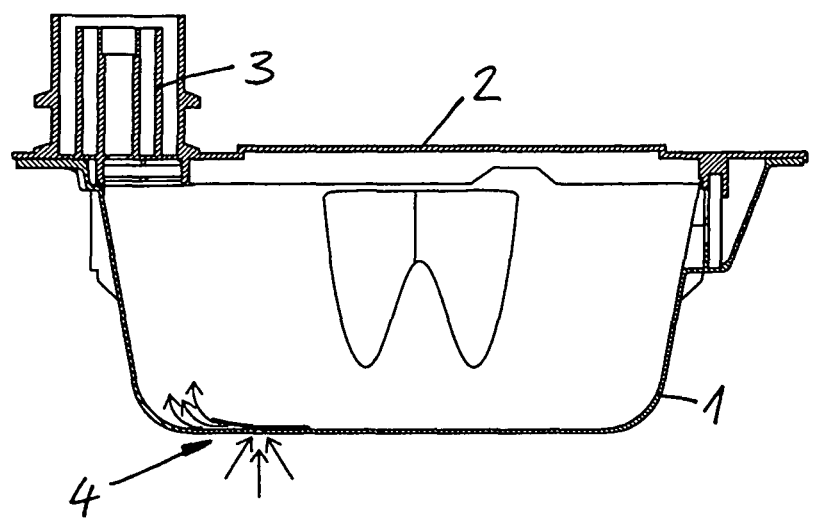
FIG. 4 is a longitudinal cross-sectional view similar to FIG. 2 with the seal member being in the process of opening.
Figure 5:
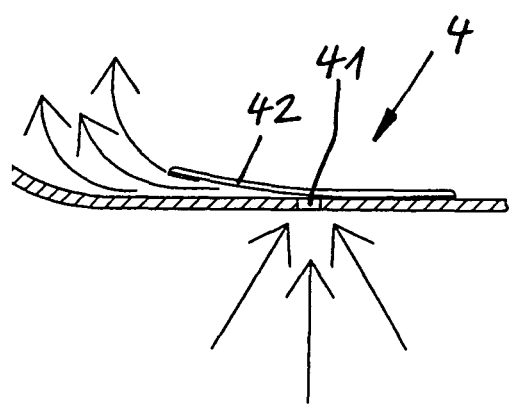
FIG. 5 is an enlarged representation of the seal area of FIG. 4 with the seal member shown in the process of opening.

During operation of the salt container in connection with a dialysis apparatus during flushing of the salt container with dialysis liquid for the absorption of the bicarbonate salt the seal member 42 is sealingly pressed by the pressure existing in the salt container onto the venting opening 41 in addition to being attached by the cement or weld joint. When the dialysis liquid is sucked out of the container however, a vacuum is generated in the salt container. If the vacuum in the salt container reaches a certain threshold value, the seal member 42 is automatically released from the bottom wall under the force of the ambient air pressure which is effective on the seal member via the venting opening 41, as shown in FIGS. 4 and 5, so that ambient air can enter the container via the venting valve 4 and the liquid can be fully sucked out of the container.

Figure 6:
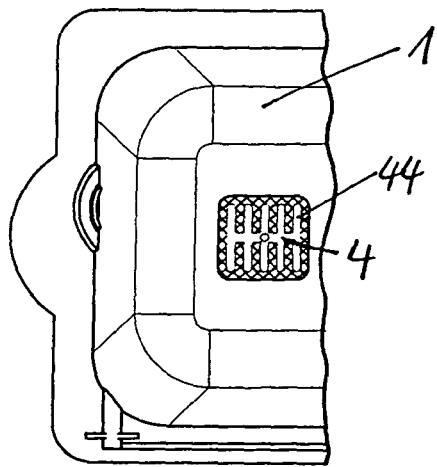
FIG. 6 is a representation similar to FIG. 1 showing a modified embodiment.
Figure 7:
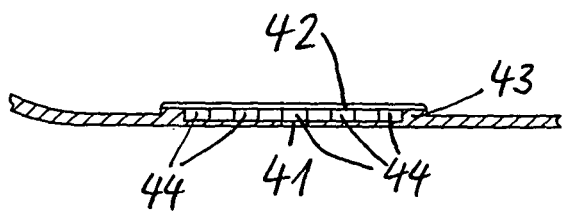
FIG. 7 is an enlarged representation similar to FIG. 3 of the embodiment modified in accordance with FIG. 6.
Figure 8:
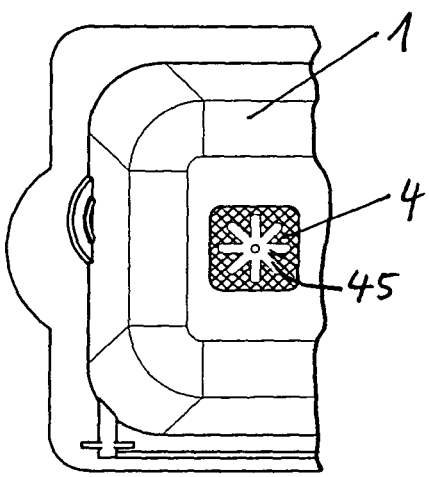
FIG. 8 is an enlarged representation similar to FIG. 1 showing another modified embodiment.
Figure 9:
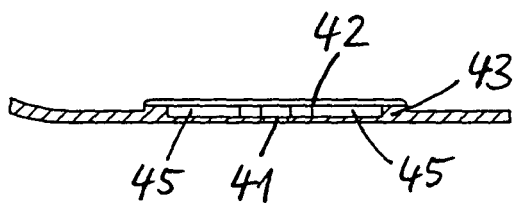
FIG. 9 is an enlarged representation similar to FIG. 3 of an embodiment modified in accordance with FIG. 8.

In representations similar to those of FIGS. 1 and 3 the FIGS. 6 and 7 as well as 8 and 9 show modified embodiments of the venting valve 4. In these modified embodiments, the bottom wall of the bottom part 1 is provided in each case with a thickened bottom wall area 43 which projects slightly upwardly for accommodating the seal member 42. In this thickened bottom wall area 43, which projects from the bottom wall surface, channel-like recesses 44 (FIGS. 6 and 7) or, respectively, 45 (FIGS. 8 and 9) are provided which, in the embodiment of FIGS. 6 and 7, have the form of a longitudinal groove with several crossing transverse grooves or which, in the embodiment according to FIGS. 8 and 9, are arranged in a star-like fashion. The raised areas remaining around these recesses are indicated in FIGS. 6 and 8 by cross-hatching and their surface areas form the cement—or, respectively, weld surface areas with the seal member 42.

While in the embodiment according to FIGS. 1 to 5, the seal member 42 must be cemented or welded to the bottom wall in a locally defined annular area with a certain distance from the venting opening 41. The cementing or, respectively, welding area must therefore be small enough so that the seal member is reliably released at a certain vacuum at least at one location. In addition, the area of the seal member subject to the ambient pressure must be larger than the cross-section of the venting opening 41. Therefore, the modified embodiments according to FIGS. 6 and 7 as well as FIGS. 8 and 9 have the advantage that the seal member 42 can be cemented or welded to the raised bottom wall area 43 over the whole raised area thereof. No particular measures are required for maintaining a predetermined cementing or welding surface area. The reason is that, with the recesses 44 or, respectively, 45 sufficiently large exposure areas of the seal member 42 to the ambient air pressure and sufficiently small cementing or welding surface areas are provided that, with an adequate vacuum in the salt container, the seal member is at least locally released.

The arrangement according to the invention forms a venting valve which is reliably closed up to the venting event, which is easy to manufacture, which has no moving parts and which does not project into the container interior, so that it is not detrimentally affected by shaking of the salt filling (for example, during transport or handling procedures) nor by the flushing of the salt container with the dialysis liquid or that it affects in any way the filling of the container with salt.

For the person skilled in the art, it is quite clear that the venting valve 4 may be arranged anywhere on the container wall, that is, instead of being arranged in the bottom part 1 of the container, it could be arranged on the cover 2. It is clear that the location for the venting valve is selected depending on the orientation of the salt container in its use position when coupled to a dialysis apparatus such that, in the use position of the salt container, the venting valve is as far as possible at the upper end of the container.

What is claimed is:

1. A hemodialysis salt container (1, 2) in the form of a single use container having rigid walls provided with a coupling arrangement (3) for establishing a flow connection with a dialysis apparatus for conducting dialysis liquid through the salt container but which is otherwise sealed in an airtight manner, said container including a venting valve (4) with a venting opening (41) formed in the container wall and a seal member (42) connected to the container wall by local cementing or welding connections so as to cover the venting opening (41) on the inside of the container wall, the cementing or welding connections being so dimensioned that, when a certain pressure difference between the ambient air pressure and a vacuum generated by the dialysis apparatus in the interior of the container is reached, the seal member (4) is at least locally ripped open.

2. A salt container according to claim 1, wherein the venting opening (41) has a small cross-section and the cementing or welding area of the seal member (42) with the container wall is disposed at a distinct radial distance from the venting opening (41).

3. A salt container according to claim 1, wherein, at the inside of the container wall in the area of the venting opening (41), recesses (44, 45) are provided which are in communication with the venting opening (41), and the seal member (42) is cemented or welded to the container wall along the wall surface areas surrounding the recesses (44, 45).

4. A salt container according to claim 3, wherein the recesses (44, 45) are formed by a geometric channel arrangement around the venting opening (41).

5. A salt container according to claim 3, wherein the recesses (44, 45) are formed by an arrangement of star-like flat channels around the venting opening (41).

6. A salt container according to claim 3, wherein, in an area corresponding to the dimension of the seal member (42), the container wall is provided with a thickened wall area projecting toward the container interior.

* * * * *